United States Patent
Zagury et al.

(12) 
(10) Patent No.: US 6,420,141 B1
(45) Date of Patent: Jul. 16, 2002

(54) ANTI-HIV IMMUNOGENS (TOXOIDS), PREPARATION METHODS AND USE FOR PREVENTING AND TREATING AIDS

(75) Inventors: Jean-Francois Zagury, Paris (FR); Jay Rappaport, Balacynwyd, PA (US); Miguel Carcagno, Buenos Aires (AR)

(73) Assignee: Neovacs (FR)

( * ) Notice: Subject to any disclaimer, the term of this patent is extended or adjusted under 35 U.S.C. 154(b) by 0 days.

(21) Appl. No.: 09/582,519

(22) PCT Filed: Dec. 14, 1998

(86) PCT No.: PCT/FR98/02727
§ 371 (c)(1),
(2), (4) Date: Mar. 15, 2001

(87) PCT Pub. No.: WO99/33872
PCT Pub. Date: Jul. 8, 1999

(30) Foreign Application Priority Data

Dec. 26, 1997 (FR) .............................. 97 16589

(51) Int. Cl.⁷ .................. C12P 21/04; A61K 39/21; A61K 38/00; C07K 1/00
(52) U.S. Cl. .................. 435/69.7; 424/208.1; 530/300; 530/350
(58) Field of Search .............................. 530/350, 300; 435/69.7; 424/208.1

(56) References Cited

FOREIGN PATENT DOCUMENTS

| WO | 8606414 | 11/1986 |
|---|---|---|
| WO | 9118454 | 11/1991 |
| WO | 9415634 | 7/1994 |
| WO | 9627389 | 9/1996 |
| WO | 9933872 | 7/1999 |

OTHER PUBLICATIONS

Copy of Abstract of No. XP–002078560 HIV–1 . . . Trail (1 page).

*Primary Examiner*—Hankyel T. Park
(74) *Attorney, Agent, or Firm*—Bierman, Muserlian and Lucas

(57) ABSTRACT

The invention concerns a viral regulation protein or a viral regulation protein fragment or the alpha interferon or the alpha interferon fragment which is carboxymethylated. The invention also concerns the preparation method and the use of the resulting product in a therapeutic method for treating the human or animal body, a pharmaceutical and vaccine composition containing, as active principle, one at least of the carboxymethylated proteins or fragments.

Figure 1:
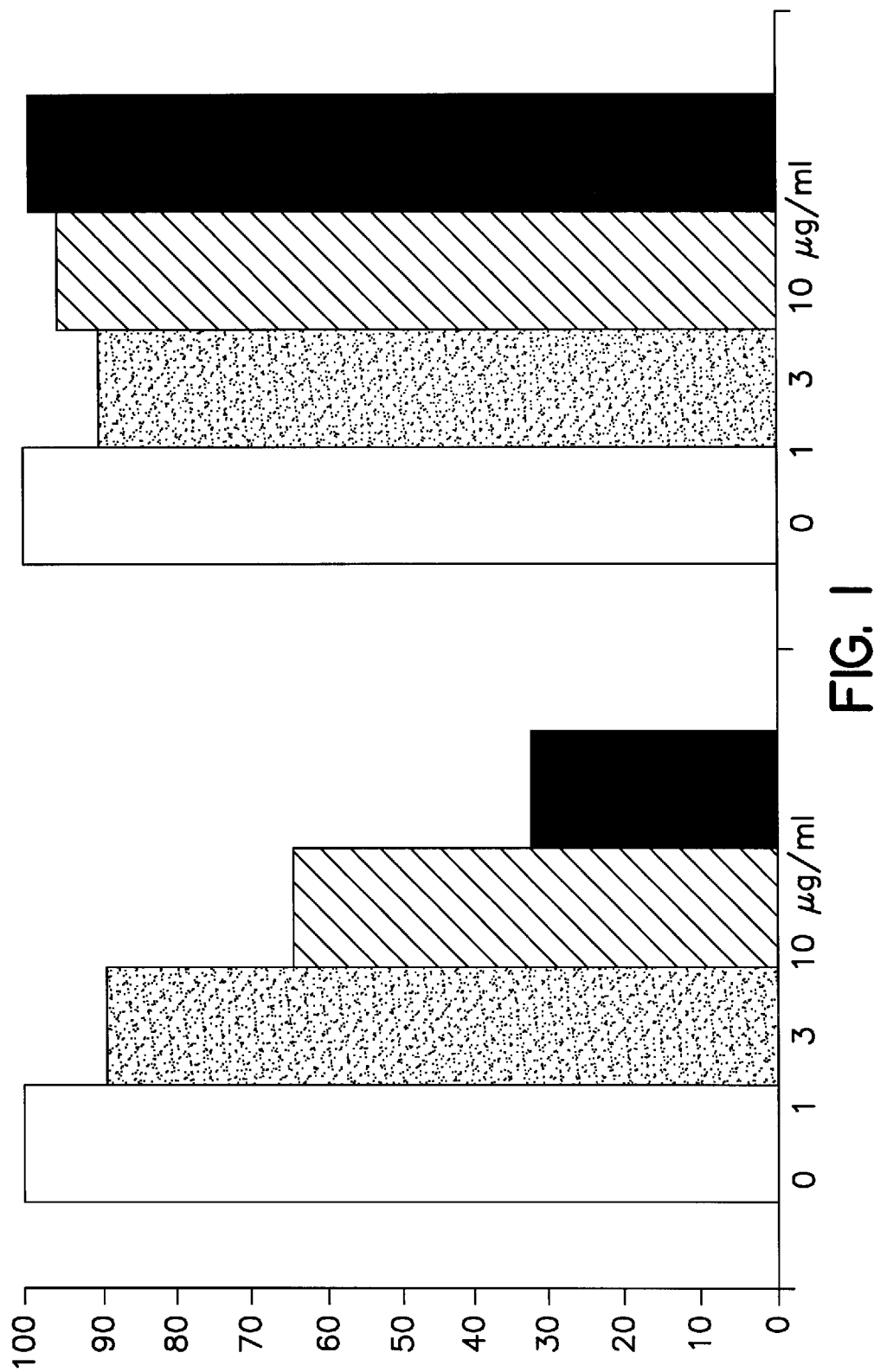

15 Claims, 1 Drawing Sheet

ANTI-HIV IMMUNOGENS (TOXOIDS), PREPARATION METHODS AND USE FOR PREVENTING AND TREATING AIDS

This application is a 371 of PCT/FR98/02727 filed Dec. 14, 1998.

Aids is induced by HIV-1 virus infection. Such virus consists in various proteins. Amongst such proteins, Tat is together with Nef protein produced the earliest in the viral cycle.

To fight against the effects of Tat protein various approaches have been proposed including genetic approaches to block Tat transcriptional action. Thus, clinical assays have taken place with antisense (Hybridon company), in vitro experiments have shown feasibility of ribozymes or mimics using the RNA of the TAR region (Tat binding site to mRNA).

Pharmacological molecules as inhibitors of Tat transcriptional effect have also been disclosed.

All these methods aim at blocking virus replication by blocking Tat transcriptional action.

Immunological methods have also been proposed for a long time.

For a specific immunization against native Tat protein, WO-A-91/18454 reports the use of polypeptides from retroviral proteins including native Tat protein, being obtained by proteolytic cleavages, chemical synthesis or genetic recombination, as immunogens to prevent the retroviral replication and the cytotoxic activity against in particular lymphocytes and nervous cells effected by retroviral proteins, in particular Tat. The toxicity of native proteins or the fragments thereof prevents however their use for an immunization.

WO-A-95/31999 reports the use of native Tat protein of HIV-1, fragments of said protein or polypeptides with deletions/substitutions as immunogens so as to block HIV-1 replication by blocking Tat extracellular protein capture by uninfected cells. In spite of the described immunogenicity, given the toxic effects of the native Tat protein in particular, the immune troubles it induces, and of the absence of neutralizing antibodies through immunization with the immunogens described therein, there is indeed a need to develop new inactivated Tat immunogens (which have lost all the nocuous effects from the native Tat protein) being adapted to induce a humoral and cellular immune response.

WO-A-96/27389 reports the use of new products, Tat toxoids and retroviral regulating proteins as immunogens adapted to induce an immune response against native Tat protein and prevent or amend the immunosuppressive effects thereof. Such toxoids, being inactive but immunogenic products, have been prepared by formaldehyde chemical treatment of the native protein or segments derived from such protein. However inactivation with aldehyde is uneasy. And for an industrial production regular results are necessary, mainly for inactivation. Moreover, Health agencies prefer products with a constant and well defined structure to authorize the sales thereof. An ideal product should further have a good stability over the time.

That is the reason why the present application aims at providing new toxoids and a simple and efficient new method to manufacture such toxoids, for example from HIV-1 regulating proteins which participate in the HIV-1 immunosuppressive effect or from alpha interferon the production of which is deranged by HIV-1 infection.

The toxoid strategy has great advantages with respect to aminoacid substitutions/deletions: the regions of native Tat protein which are responsible for the Tat pleomorphic effects are not well identified and it is difficult to predict a priori the substitutions/deletions which provide a total innocuity for the preparation thereof. For example mutation of C25 residue in G cancels Tat transactivating effect without suppressing the immunosuppressive effect thereof. On the other side, substitutions/deletions may alter strongly the structure of the modified molecule with respect to the native molecule (linear and conformational antigens) and thus prevent the development of an efficient immune reaction against the native molecule. This last point is particularly important for generating neutralizing antibodies against native protein.

An object of the present application is thus to provide a viral regulation protein or a fragment of a viral regulation protein or alpha interferon or a fragment of alpha interferon, characterized in that it is carboxymethylated.

In preferred implementation conditions for the invention, the above-mentioned protein or fragment comes from HIV-1, HIV-2, HTLV-1 or HTLV-2 virus, particularly HIV-1 or HIV-2 virus.

In other preferred implementation conditions for the invention, the above-mentioned protein or fragment is a viral regulation protein or a fragment of a viral regulation protein.

In further preferred implementation conditions for the invention, the above-mentioned protein or fragment comes from Tat, particularly from HIV-1.

Another object of the present application is also to provide a process for producing a protein or a fragment such as defined here-above, characterized in that said viral regulation protein or said fragment is submitted to a carboxymethylation step to obtain the expected compound which is isolated.

According to the invention, the proteins or fragments which have the same behaviour as toxins on the immune system, either the overproduced IFNα, Tat or Nef, for example are modified with the carboxymethylation. Such chemical modification leads to new proteins or fragments which are biologically inactive, but hold their immunogenicity. In other words, such proteins or fragments which have the same behaviour as toxins on the immune system are recognized by antibodies produced against the carboxymethylated proteins or fragments according to the invention. Such carboxymethylated proteins or fragments hold enough immunogenic properties to create antibodies neutralizing or blocking said native protein and simultaneously have lost at least 90%, preferably at least 95%, more preferably at least 99% of the toxic biological properties of said native protein, namely its well known usual biological properties.

The carboxymethylated immunogenic compound according to the invention may consist in the totality or a fragment of the protein, including regulation protein, and may comprise, as it is well known by the skilled man in the art, one or more modifications in the aminoacids of such protein or fragment such as deletions, substitutions, additions or finctionalizations such as acylating aminoacids, inasmuch such modifications stay in the above-mentioned limits (no toxicity, immunological characters). For example, generally substituting an isoleucine residue for a leucine residue does not modify such properties. The modifications should generally concern less than 30% aminoacids, preferably less than 20%, more preferably less than 10%.

A fragment may comprise from 8 to 110 aminoacids for example, preferably from 12 to 60 aminoacids, more preferably from 12 to 40 aminoacids. Such a fragment may also comprise on the C- or N-terminal side(s) from 1 to 5 supplementary aminoacids, i.e. different from the origin segment. A fragment should also comprise one cystein at least to allow for carboxymethylation.

Generally, as to the modifications, the homology or similarity between the modified immunogene and the protein or part of native protein as well as the dimensions of the immunogenic compound and the use procedures or coupling of the immunogenic compound according to the invention with an immunogenic protein such as the tetanus toxoid, it may be referred in particular to equivalent WO-A-86/06414 or EP-A-0,220,273 or further PCT/US.86/0083 1 the teaching of which is incorporated therein by reference.

The immunogenic compounds according to the invention derived from regulation proteins will be called sometimes below in the experimental part "viral toxoids".

In fact, as for the conventional bacterial toxoids, they are free from own toxicity, but are adapted to provoke an immunization per administration to a subject.

To verify that the native regulation protein is well recognized by antibodies raised against said modified regulation protein, it is possible for example to check immunologically through Elisa in the presence of specific antibodies, the building of antigen-antibody complexes, as it will be shown below in the experimental part.

To see if the immunogenic properties of the regulation protein have been sufficiently preserved to create antibodies neutralizing said native protein, it is possible for example to immunize mammals (rabbits, rats, mice) with an immunogenic compound according to the invention and check that the produced antibodies for neutralizing the toxic activities for the Tat.

To check if the modified regulation protein has lost at least 90% of its toxic biological properties, it is possible for example as to the Tat to study the effect of the inactivated Tat on the immunosuppression of T cells or the neoangiogenesis.

Inactivation of Tat regulation protein is checked for example by the "Tat Rescue Assay" by using a non infectious Tat deficient HIV mutant cultured on cell line HL-1 the replication of which depends upon an exogenous supply of native Tat.

The immunogenic compound according to the invention may derive particularly from any one of regulation proteins of the HIV-1, HIV-2, HTLV-1 or HTLV-2 viruses, including Nef, Rev, preferably Tat, of the HIV-1 and HIV-2 viruses.

The Tax protein of HTLV-1 or HTLV-2 may also be mentioned.

An object of the present application is also to provide a process for producing a protein or a fragment such as defined above, characterized in that said viral regulation protein or said fragment is submitted to a carboxymethylation step to obtain the expected compound which is isolated if desired.

The carboxymethylation reaction allows to modify the thiol groups (sulfhydryl group) being present at the cystein residues of the aminoacids chain. Such groups react with iodoacetic acid or iodoacetamide by a S-carboxymethylation or S-carboxyamidomethylation reaction, respectively.

For example, Tat protein has 7 cysteins. Such cysteins participate in the building of inter- and intra-chain disulfide bridges and assist oligomer formation.

The reaction product is in any case a S-carboxymethylcysteinyl or S-carboxymethylamidocysteinyl residue.

The carboxymethylation reaction may also be carried out with other chemical agents like performic acid, 3-bromopropionic acid, ethyleneimine, (2-bromoethyl) trimethyl ammonium bromide, 2-bromoethane sulfonate, 1,3-propanesulfone, etc.

In preferred implementation conditions for the above-mentioned process, said starting protein or fragment is under the form fused with a marker (FP) when it is submitted to carboxymethylation.

The starting proteins or fragments of the process are known products described in the literature, for example for Tat from HIV-1 by Frankel A. D. et al. (Cellular uptake of the tat protein from human immunodeficiency virus, Cell, 1988, 55:1189–93) or for Nef from HIV-1 by Azad A. A et al. (Large-scale production and characterization of recombinant human immunodeficiency virus type 1 Nef, J. Gen. Virol. 1994, 75:651–55), or could be prepared conventionally.

Starting proteins or fragments above-described may be in particular prepared:

1) by synthesis through genetic engineering or by biochemical synthesis, 2) by purification.

Genetic engineering allows to purify the proteins produced by affinity chromatography by using for example antibodies raised against the protein or one of the fragments thereof; the protein fused with a marker (FP) which will be used as an anchor for an affinity column may be also synthetized.

In other preferred implementation conditions for the above-mentioned process, when the protein or fragment is fused with a marker (FP), it is submitted to:

a concentration step, for example by ultrafiltration, a desalting step for example by gel filtration, a treatment with cyanogen bromide or enterokinase to cleave the fusion protein and thus release the protein or fragment, concentration and diafiltration steps, a chromatography by cationic exchange, a concentration step by ultrafiltration followed by an exclusive gel filtration.

The above-mentioned cyanogen bromide reaction allows to cleave the thioethers. The cyanogen bromide reaction on the polypeptide molecules is selective by carrying out a cleavage at the existing methionine residues. Such a reaction ends to the formation of two polypeptide fragments per methionine residue. Such a reaction may be advantageously coupled with the above-described carboxymethylation reaction, but it is not necessary for the inactivation.

In other preferred implementation conditions for the above-mentioned process, the expected protein or fragment coupled with a compound to allow its purification, for example with a peptide fragment containing various histidines, preferably in a continuous sequence of 4, 5, including 6 histidines or more to allow the fixation with a nickel column is prepared. Inasmuch the presence of such a compound does not induce toxicity and does not modify disadvantageously the immunogenicity of the protein or the fragment, it is not necessary to cleave it after purification. However, in these preferred implementation conditions, such compound is cleaved to eliminate it.

The compounds that are the objects of the present invention have very interesting pharmacological properties. They are biologically inactive with respect to the functions they perform usually such as the immunosuppressive effects, the transactivating effects of the HIV-1 promotor or the oxidative effects for Tat, the anti Vesicular Stomatitis Virus (VSV) effects on the MDBK system or the immunosuppressive effects for the IFN-α.

They are immunogenic for mice, but also for human beings. They allow in particular the induction of a humoral immune response with neutralizing antibodies and a cellular immune response.

Such properties are illustrated below in the experimental part. They justify the use of the above-mentioned proteins or fragments as well as the addition salts thereof with pharmaceutically acceptable acids as a medicament.

That is the reason why the invention also aims at a carboxymethylated protein or fragment as described above, for its use in a therapeutic treatment method for the animal or human body, i.e. as a medicament.

The medicaments according the present invention find their use for example in the curative as well as preventive treatment of the harmful effects caused by an overproduction of IFN-α or a viral regulation protein, including a retrovirus HIV-1, HIV-2, HTLV-1 or HTLV-2.

The Tat and Nef proteins have quite well preserved regions. However, the case being, the same patient will be able to be immunized with toxoids prepared from varying strains, including to adapt itself to geographic variations of the epidemic.

The immunogenic compounds according to the invention may be used as follows:

A patient requiring such a treatment is administered with an immunogenic compound according to the present invention, for example subcutaneously or intramuscularly, in a sufficient quantity to be efficient therapeutically. The administered dose may range for example from 50 to 1000 μg intramuscularly as a e/h emulsion once a month during three months, and then periodically depending upon the induced serum antibody rate, for example every 2–6 months.

As medicaments, the carboxymethylated proteins or fragments from above may be incorporated to pharmaceutical compositions adapted for oral and mainly parenteral administration.

A composition according to the invention may be administered through any conventional way being used in the vaccine field, in particular subcutaneously, intramuscularly, intravenously or orally. The administration may be carried out in a single dose or in a repeated dose one or more times after a certain period of time.

The invention has also as an object to provide pharmaceutical compositions comprising at least an above-mentioned compound as an active ingredient.

In such compositions, the active ingredient is advantageously present in physiologically efficient doses; said compositions contain for example an efficient immunogenic dose of at least an active ingredient as described above. The immunogenic compound may be packaged alone or in a mixture with a pharmaceutically acceptable excipient such as a builder.

Such pharmaceutical compositions may be for example liquid and present under the pharmaceutical forms currently used in human medicine for the vaccines, like for example the injectable preparations including as an emulsion; they may be prepared according to the usual methods. The active ingredient(s) may be incorporated to the excipients usually used in such pharmaceutical compositions, such as aqueous carriers, calcium phosphate, alum, . . .

The invention aims including at pharmaceutical compositions such as:
  a) a pharmaceutical composition comprising as a preventive or curative agent a viral toxoid or a fragment or similar of a regulation protein, for example Tat, according to the invention,
  b) a pharmaceutical composition comprising as a preventive or curative agent anti-Tat antibodies produced from organisms immunized against such protein or the fragments thereof F(ab')2 or Fab according to the invention.

The present invention aims thus at a process for preparing an above-mentioned composition, characterized in that the active ingredient(s) are mixed, according to known methods per se, with acceptable excipients, including pharmaceutically acceptable ones.

Moreover, the invention concerns a kit comprising a vaccine pharmaceutical composition which, besides the active ingredient (for example Tat toxoid or derivatives or anti-Tat antibodies thereof), may comprise a builder and/or another immunogene with anti-retrovirus properties.

Another immunogene may include for example the envelope protein GP 160, including the transmembrane glycoprotein GP 10 of HIV-1 or the known fragments thereof in the state of art, the Gag protein of the viral capsid or even the Pol protein.

The invention aims finally at the use of an above-mentioned carboxymethylated protein or fragment so as to obtain a medicament adapted for a use as an immunogene.

The following examples illustrate the present application.

FIG. 1 shows the results of the evaluation of the effects of native Tat compared to those of the product of example 1 on the proliferation of normal lymphocytes being stimulated by a booster antigen.

Preparation A 2 ml are cultured of the bacteria deposited at the Collection Nationale de Cultures de Microorganismes de Paris on the $26^{th}$ of December 1997 under the number no. I-1964 which is an *E. coli* bacteria wherein there is inserted through transfection a recombinant plasmid containing a gene encoding a polypeptide comprising a fragment consisting in 6 histidines, associated with the gene of Tat protein, in 400 ml of a base culture medium (yeast extract 5 g/l, tryptone 1 g/l, sodium chloride 1 g/l) and 40 ml of a solution 1 ($CaCl_2 2H_2O$: 0.175 g/l, $MgSO_4 7H_2O$: 5.9 g/l, glucose: 6 g/l). The culture is thereby incubated at 30° C. during 10 hours at 250 rpm.

The above-mentioned pre-fermentation is followed by a fermentation in analogous conditions by maintaining the oxygen level dissolved at a saturation level of 70% by regulating stirring. When the optical density measured at 650 nm reaches a value of 6, 100 ml of a sterile 3.75% ITPG (isopropyl β-d-thiogalactopiranoside) solution are added to deionized water. Simultaneously, the medium is supplemented with a sterile 25% yeast extract solution. A solution is then added comprising $MgSO_4 7H_2O$: 8.5 g/l, glucose: 300 g/l, $(NH_4)_2SO_4$: 106 g/l, trace elements, maintaining the glucose concentration beyond 2 g/l. The bacterial mass is then cropped 4 hours after IPGT introduction. A diafiltration is then carried out against a buffer of Tris 0.1 M, $NaH_2PO_4$ 0.1 M, dithiothreitol 1 mM, pH 8.0, by counter-current filtration (threshold 0.3 μm).

Three litres of the above-mentioned raw product are lysed with 4 passes at an overpressure of 500 bars. The lysate is then centrifugated during 15 min at 4° C. and 5000 rpm. The supernatant is then added with a sufficient quantity of urea to obtain an 8 M solution and the pH is adjusted to 8.

A purification is then carried out by affinity chromatography on a nickel-NTA agarose column (Qiagen) previously balanced with 600 ml buffer A (urea 8 M, $NaH_2PO_4$ 0.1 M, Tris-HCl 0.1 M , DTT 1 mM, pH 8.0). Once loaded, the column is washed out with 250 ml buffer A. The protein is then eluted by using a discontinuous gradient to obtain the expected fused protein.

The resulting solution is concentrated on an Amicon membrane with a cutoff of 3000 daltons to obtain a final concentration of 10 mg/ml. An eluate is thus obtained comprising the expected HIV-1 recombinant fused protein Tat.

Thus, a fusion protein Tat fused genetically with a histidine-rich peptidic fragment allowing for its tying to the nickel for a purification is obtained.

The so-obtained eluate will be submitted to the carboxymethylation reaction.

EXAMPLE 1

Preparation of Tat Toxoid

Step A: Carboxymethylation

A solution of the TAT protein fused with a histidine-rich peptidic fragment prepared in the above-mentioned preparation 1 is adjusted to obtain the following concentrations: Urea 8 M, Tris-HCl 0.3 M, dithiothreitol 10 mM, pH 8.4.

Under an inert atmosphere, 2.6 g iodoacetic acid are added to 100 ml of the above-mentioned solution. Such a solution is incubated at 37° C. in a light-free environment and under an inert atmosphere during 90 min. The reaction is blocked by adding 1 ml of 98% β-mercaptoethanol and the incubation is continued during 60 minutes in the same conditions as above.

The solution resulting from the previous step is concentrated with an Amicon concentrator (Cat #8400) on an YM3 membrane (cutoff of 3000 D) up to a concentration of 10 mg/ml.

It is then desalted by passing it in a Cellufine GH25 (MATREX) column balanced with 300 ml of an urea solution 4 M, HCl 0.1 M.

Step B—Purifications

The eluate is then ultrafiltrated and treated with cyanogen bromide so as to cleave the amino terminal part of the carboxymethylated product at the level of methionine. Cyanogen bromide is added in excess under an inert atmosphere in a quantity of about 50 moles cyanogen bromide per mole of methionine. This solution is preserved in a closed container during 24 hours at 37° C. The cyanogen bromide excess is removed by evaporation under a reduced pressure.

The resulting solution is then concentrated, diafiltrated against a buffer formed with acetic acid and sodium acetate 0.05 M, pH 5, by using an Amicon diafiltrator provided with an YM3 membrane (cutoff of 3000 kD). The quantity of inactive product being obtained in solution is about 450 mg.

Such solution is filtrated on an ion-exchange SP-Sepharose FF column previously balanced with 200 ml buffer A and the product is eluated by a NaCl gradient.

The eluate is again concentrated by diafiltration in the same Amicon system and the obtained fraction is purified by gel filtration on a Sephacryl S column (Pharmacia) balanced with a phosphate buffer at pH 7.4. The final product is filtrated on a 0.22 µm membrane and stored at 4° C. until use.

Such product has been subjected to the analyses mentioned below and to pharmacological tests.

Analyses

Total quantity of inactivated product dosed with Bradford test: 150 mg.

Electrophoresis on polyacrylamide gel SulfoDodecylSulfate-PAGE, silver coloration (Phast System, Pharmacia, 20% homogenous gel): a single band with a molecular weight compatible with the one expected. No other bands detectable at higher or lower weights.

Electrophoresis by isoelectric gradient (Phast System, Pharmacia, GEL IEF 3-9): a single band visible.

Western blot (Phast System, Pharmacia, monoclonal antibody to hybridome 5G11): a single band observed and no material aggregated or degradated.

Biological activity (induction of the gene CAT in the line HELA-HIV-1-LTR CAT): no activity detectable.

N-terminal part sequencing by using the Edman standard sequencing technique with an Applied Biosystems sequencer (477A model): the resulting first 20 aminoacids coincide with the expected sequence:

E-P-V-D-P-R-L-E-P-W-K-H-P-G-S-Q-P-K-T-A

Endotoxines (LAL test according to USP XXIII protocol): less than 0.5 endotoxic unit per mg of protein.

Sterility (according to USP XXIII protocol): suits to the standards.

Substitution degree measurement: by using Ellman reactant to determine the free sulfhydryl groups by comparison with a standard curve measuring the cysteins. By comparing the native Tat with the carboxymethylated Tat, it has been found that only 0.03% of the cysteins held their activity in the carboxymethylated Tat, i.e. 1 active cystein for 3330 inactive cysteins. A simple calculation shows that, to reach one Tat molecule with 7 active cysteins under these conditions, several kg of Tat protein would be necessary. Inactivation is thus quasi total.

EXAMPLE 2

Preparation of Nef Toxoid

For cloning, Nef primers are used for obtaining the Nef gene through RT-PCR from RNA of HIV-1 infected cells. Then the same plasmid with the same lysine-rich fusogenic segment which allows the tying onto the nickel column being used. The production and purification protocol is then the same as in example 1, but cutting is carried out by the action of enterokinase and not cyanogen bromide.

The analysis results are similar to those obtained with Tat protein.

EXAMIPLE 3

Preparation of IFN-α Toxoid

This time, the plasmid does not use any fission protein. The protein is produced such as by genetic engineering with no fusogenic segment and is purified by using a chromatographic column with which monoclonal antibodies anti-IFN-α are tied. When eluted, the protein is immediately inactivated according to the same protocol as the one described in example 1.

The analysis results are identical to those obtained with the Tat protein with a biological test showing an zero antiviral activity (VSV virus on MDBK cells): the biological inactivation is total.

PHARMACOLOGICAL STUDY

1) Absence of an Immunosuppressive Effect of Tat Toxoid

There is a simple test showing the immunosuppressive effect of the native Tat protein. Peripheral blood cells (PBMC) are incubated in a no-serum medium with native Tat protein or Tat toxoid in concentrations varying from 0 to 10 mg/ml. After a 2 hour contact, serum is added up to a 10% final concentration and cells are stimulated as usual with Staphylococcus Enteroxin B (SEB) or a booster antigen Protein Purified Derived (PPD). Proliferation is evaluated after three days SEB or 5 days PPD.

It can be seen that proliferation is reduced depending upon the dose with the native Tat whereas it is not with the toxoid.

On FIG. 1, the 4 bars on the left correspond to the native Tat and the 4 bars on the right correspond to the compound according to the example 1 (Tat toxoid). The figures on the abscissa are the product concentrations in μg/ml, respectively 0, 1, 3, 10 μg/ml. The ordinates show the cell T proliferation in percentage. The control corresponds to a Tat concentration being used equal to zero. It can be seen that the native Tat inhibits the cell proliferation whereas the compound according to the example 1 has no effet.

2) Immunogenicity of Tat Toxoid in Mice, Production of Neutralizing Antibodies

A Tat toxoid prepared according to the example 1 has bee used to immunize mice. The immunization protocol is the one conventionally used: mice are injected intramuscularly (im) with 100 μl emulsion (1:1) in a complete Freund's adjuvant containing 20 μg product at day 0 with a booster in an incomplete Freud's adjuvant of 5 μg at days 21 and 35. The serum is taken out from mice at days-2, 28 and 40 and the anti-Tat antibodies are measured through ELISA on plates sensibilized with native recombinant Tat protein (chemically untreated) or with a compound according to the example 1. The sera have been tested at a 1/1000 dilution. The obtained results expressed in optical density on 3 immunized mice (1 to 3) and 3 non immunized mice (4 to 6) are shown on the following table:

|         |      | Native Tat | Toxoid Tat |
|---------|------|------------|------------|
| Mouse 1 | D -2 | 0.3        | 0.3        |
|         | D 28 | 1.6        | 1.5        |
|         | D 40 | 2          | 2.1        |
| Mouse 2 | D -2 | 0.2        | 0.3        |
|         | D 28 | 1.9        | 1.8        |
|         | D 40 | 2.2        | 2.2        |
| Mouse 3 | D -2 | 0.4        | 0.4        |
|         | D 28 | 1.7        | 1.5        |
|         | D 40 | 1.9        | 2.2        |
| Mouse 4 | D -2 | 0.2        | 0.2        |
|         | D 28 | 0.3        | 0.2        |
|         | D 40 | 0.3        | 0.3        |
| Mouse 5 | D -2 | 0.4        | 0.4        |
|         | D 28 | 0.4        | 0.3        |
|         | D 40 | 0.3        | 0.3        |
| Mouse 6 | D -2 | 0.3        | 0.3        |
|         | D 28 | 0.4        | 0.3        |
|         | D 40 | 0.3        | 0.3        |

Such results show that mice immunized with the toxoid produce antibodies recognizing similarly the native protein and the toxoid.

These antibodies are moreover neutralizing. That has been established with 2 different tests:

Inactivation test of the Tat protein. There are added to culture cells of the HELA-HIV-1-LTR-CAT line, which are stably transfected with a HIV-1 Long Terminal Repeat (LTR) containing plasmid as Chloramphenicol Acetyl Transferase (CAT) gene promotor, native Tat protein or Tat toxoid, or native Tat protein pre-incubated 1 hour with serum (1/50 dilution) from mouse (D 0 or D 40) immunized or not. The native Tat protein at 5 μg/ml enters the cells and will play its transactivating role on the HIV-1 LTR and induce the expression of CAT protein. After 48 hours, cells are lysed and the CAT protein quantity being present is measured with an ELISA test (Boehringer). The results are expressed in optical density (OD):

|                          | Mouse number/day | OD (CAT protein value measured) |
|--------------------------|------------------|---------------------------------|
| Native Tat               |                  | 1.4                             |
| Toxoid Tat               |                  | 0.2                             |
| Native Tat + mouse serum | 2/D 0            | 1.5                             |
| Native Tat + mouse serum | 6/D 0            | 1.3                             |
| Native Tat + mouse serum | 2/D 40           | 0.3                             |
| Native Tat + mouse serum | 6/D 40           | 1.4                             |

Such results show that immunized mouse serum (mouse 2) contains antibodies neutralizing the native Tat protein, which is not the case for a non immunized mouse.

Also, if antibodies produced by mice immunized with the toxoid in the immunosuppression test described in the pharmacological study 1) above (dilution 1/50) are used, the immunosuppressive effect of the native Tat protein is blocked.

All those results show that the compound according to example 1 is immunogenic and allows to induce an immune response which neutralize the native protein.

3) Immunogenicity of IFN-α Toxoid in Mice, Production of Neutralizing Antibodies A IFN-α toxoid prepared according to the example 3 has been used to immunize mice. The immunization protocol is the one conventionally used: mice are injected (im) with 100 μl emulsion (1:1) in a complete Freund's adjuvant containing 20 μg product at day 0 with a booster in an incomplete Freud's adjuvant of 5 μg at days 21 and 35, 45. The serum is taken out from mice at days-2, 28 and 50 and analysed through ELISA on plates sensibilized with native recombinant IFN-α protein (chemically untreated) or with the toxoid. The sera have been tested at a 1/1000 dilution. The obtained results expressed in optical density on 3 immunized mice (1 to 3) and 3 non immunized mice (4 to 6) are shown on the following table:

|         |      | Native IFN-α | Toxoid IFN-α |
|---------|------|--------------|--------------|
| Mouse 1 | D -2 | 0.3          | 0.3          |
|         | D 28 | 1            | 0.9          |
|         | D 50 | 2.1          | 2.1          |
| Mouse 2 | D -2 | 0.2          | 0.3          |
|         | D 28 | 1.2          | 1.1          |
|         | D 50 | 1.9          | 2            |
| Mouse 3 | D -2 | 0.4          | 0.4          |
|         | D 28 | 0.8          | 0.9          |
|         | D 50 | 2            | 2.1          |
| Mouse 4 | D -2 | 0.1          | 0.1          |
|         | D 28 | 0.2          | 0.2          |
|         | D 50 | 0.1          | 0.1          |
| Mouse 5 | D -2 | 0.2          | 0.2          |
|         | D 28 | 0.2          | 0.2          |
|         | D 50 | 0.2          | 0.3          |
| Mouse 6 | D -2 | 0.3          | 0.3          |
|         | D 28 | 0.2          | 0.3          |
|         | D 50 | 0.3          | 0.3          |

Such results show that mice immunized with the toxoid produce antibodies recognizing similarly the native protein and the toxoid. On the other side, that confirms the safety for the immunization through IFN-α toxoid, because the mice have well tolerated the immunization.

These antibodies are moreover neutralizing. That has been established through the conventional test of using VSV viruses on the MDBK cells. Normally by adding from 1 to 10 interferon units, the cells are made lysis-resistant with VSV virus. By incubating native IFNα with serum from mouse 1 or 4 (D 0, D 50) diluted at 1/50, lysis is observed only when the native IFN(X has been pre-incubated with serum from mouse 1 at D 50.

This example shows that the compound of example 3 is immunogenic while forming neutralizing antibodies.

4) Immunogenicity of Nef Toxoid in Mice

Nef toxoid prepared according to example 2 has been used to immunize mice. The immunization protocol is the one conventionally used: mice are injected (im) with 100 µl of an emulsion (1:1) in a complete Freund's adjuvant containing 20 µg product at day 0 with a booster in an incomplete Freud's adjuvant of 5 µg at days 21 and 35. The serum is taken out from mice at days-2, 28 and 40 and analysed through ELISA on plates sensibilized with native recombinant Nef protein (chemically untreated) or with the toxoid of example 2. The sera have been tested at a $^1\!/_{1000}$ dilution. The obtained results expressed in optical density on 3 immunized mice (1 to 3) and 3 non immunized mice (4 to 6) are shown on the following table:

|  |  | Native Nef | Toxoid Nef |
|---|---|---|---|
| Mouse 1 | D −2 | 0.1 | 0.1 |
|  | D 28 | 1 | 0.9 |
|  | D 50 | 2.1 | 2.1 |
| Mouse 2 | D −2 | 0.1 | 0.1 |
|  | D 28 | 1.5 | 1.4 |
|  | D 50 | 1.9 | 2 |
| Mouse 3 | D −2 | 0.1 | 0.1 |
|  | D 28 | 0.8 | 0.9 |
|  | D 50 | 1.6 | 1.6 |
| Mouse 4 | D −2 | 0.1 | 0.1 |
|  | D 28 | 0.1 | 0.1 |
|  | D 50 | 0.1 | 0.1 |
| Mouse 5 | D −2 | 0.1 | 0.1 |
|  | D 28 | 0.1 | 0.1 |
|  | D 50 | 0.1 | 0.1 |
| Mouse 6 | D −2 | 0.1 | 0.1 |
|  | D 28 | 0.1 | 0.1 |
|  | D 50 | 0.1 | 0.1 |

Such results show that mice immunized with the toxoid of example 2 produce antibodies recognizing similarly the native protein and the toxoid. On the other side, that confirms the safety for the immunization through Nef toxoid, because the mice have well tolerated the immunization.

5) Effect of Antibodies from Mice Immunized with Tat and IFNα Toxoids on the Infection with HIV-1 in Vitro An immunosuppressive test induced by the infection HIV-1 in vitro has been developed. This test is performed as follows.

Peripheral blood cells (PBMCs) of a healthy subject are infected with a lymphotropic HIV-1 strain (HIV-HTLVIIIB). After a stimulation with Phytohemagglutinin (PHA) and a culture during 6 days in the presence of interleukin-2, cells are irradiated. The irradiated cells are suppressive, because they are able to inhibit proliferation of autologous PBMCs being stimulated by antigens like SEB or PPD. Such immunosuppressive effect is not bound with residual virus after irradiation, because the tests for dosing inverse transcriptase or p24 antigen in the supernatants are negative. If a preparation is made of virus-free cells (control) being irradiated on the same way 6 days after a stimulation with PHA and they are added to autologous cells stimulated with SEB or PPD, no proliferation inhibition is observed. The inhibiting effect is due to HIV-1 virus.

J. F. Zagury et al. (Cell Pharmacol. AIDS Sciences, 1996, Vol. 3, pp. 97–103, A critical role of the Tat and IFNα in the HIV-1 induced immunosuppression leading to AIDS) describes that the genesis of these suppressive cells depends both upon IFNα and Tat protein, since antibodies neutralizing those 2 proteins prevent suppressive cells from being formed. When, in such an experiment, sera (diluted at $^1\!/_{50}$) from mice immunized with the products described in examples 1 and 3 (Tat toxoid and IFNα toxoid) are added simultaneously, such sera block the generation of suppressive cells. That is not the case with sera from non immunized mice (negative control) or with sera taken before any immunization. If serum from mice immunized with Tat toxoid only is used, immunosuppression is not blocked any more. On the contrary, when serum from mice immunized with IFNα toxoid is used, suppression inhibition is 70%. If both anti-Tat and anti-IFNα sera are combined, the genesis of suppressive cells is completely blocked. Such results have been obtained by using various batches of viruses, including primary isolates. This shows that anti-Tat antibodies obtained with only one toxoid can also have a cross reactivity.

J. F. Zagury et al. (Cell Pharmacol. AIDS Sciences, 1996, Vol. 3, pp. 97–103, A critical role of the Tat and IFNα in the HIV-1 induced immunosuppression leading to AIDS) confirm the combined inhibitor effect of Tat and IFNα with respect to the immunosuppressive effect in patients infected with AIDS. Moreover, they confirm the initiator role of Tat and the determining role of IFNα in such an immunosuppression (see D. Zagury et al. publication (IFN and Tat involvement in the immunosuppression of uninfected T cells and C-C chemokine decline in AIDS, Proc. Natl. Acad. Sci. USA, 1998, being printed). The results of such works show the need to fight against the ellular Tat protein by induction of a neutralizing antibody response by vention if possible from the Tat production by induction of a cellular nue response.

6. Imunogenicity and Safety of Tat and IFNα Toxoids Combined or not in Humans. Compatibility with Chemotherapy Tables 1, 2, 3 describe the results obtained upon a phase 1 test using toxoids from examples 1 and 3 in a 50—50 emulsion with ISA 51 (SEPPIC): 1 ml me containing 100 µg active agent according to the invention. The responses to the IFNα toxoid (data not illustrated here) are similar to those already described in publications of Gringeri et al. in JAIDS 1994, Vol. 7, 978–988, and Vol. 13, 55–67 about a toxoid prepared by formolation.

Table 1: Description of patients included in the phase 1 test.

Table 2: Biological parameters at initial and final times (generally over 6 months).

Table 3: Analysis of anti-Tat specific response.

TABLE 1

Demography of patients immunized against HIV-1 Tat, age at the seroconversion and antiretroviral treatment time

| Code | Age | Sex | Risk factor | Age at seroconversion time | Antiviral treatment | with proteinase | Anti-IFNα immunization |
|---|---|---|---|---|---|---|---|
| 1 | 25 | M | Hemophilic | 12 | Y | Y | Y |
| 2 | 39 | M | Hemophilic | 26 | N | N | N |

TABLE 1-continued

Demography of patients immunized against HIV-1 Tat, age at the seroconversion and antiretroviral treatment time

| Code | Age | Sex | Risk factor | Age at sero-conversion time | Antiviral treatment with proteinase | Anti-IFNα immunization |
|---|---|---|---|---|---|---|
| 3 | 33 | F | Sexual partner | 26 | Y | Y | Y |
| 4 | 38 | M | Hemophilic | 23 | N | N | Y |
| 5 | 25 | M | Hemophilic | 12 | N | N | N |
| 6 | 31 | M | Hemophilic | 19 | Y | N | N |
| 7 | 19 | M | Hemophilic | 7 | N | N | Y |
| 8 | 35 | M | Hemophilic | 22 | Y | N | Y |
| 9 | 26 | M | Hemophilic | 15 | N | N | N |
| 10 | 38 | M | Hemophilic | 26 | N | N | N |
| 11 | 26 | M | Hemophilic | 14 | Y | Y | N |
| 12 | 33 | M | Hemophilic | 20 | Y | Y | N |
| 13 | 40 | F | Sexual partner | 36 | N | N | N |
| 14 | 26 | F | Sexual partner | 20 | N | N | Y |

TABLE 2

Counting of CD4 cells in absolute value, HIV-1 plasmatic viremia and antigenemia in 14 seropositive patients immunized with products from example 1 or 3

| Code | Followed in months | Counting of CD4 cells in cells/mm³ Before | After | HIV-1 viremia Basal | After | Anti-HIV antigens Basal | After |
|---|---|---|---|---|---|---|---|
| 1 | 8 | 284 (28.4%) | 345 (34.5%) | 5.75 | 5.71 | 11 | 4 |
| 2 | 8 | 453 (16.8%) | 534 (18.4%) | 2.06 | 2.15 | 32 | 3 |
| 3 | 12 | 227 (28.4%) | 345 (34.5%) | 0.35 | <0.005 | 17 | 4 |
| 4 | 3 | 287 (22.1%) | 252 (21.0%) | 0.49 | 0.70 | 3 | 3 |
| 5 | 5 | 282 (28.2%) | 319 (22.8%) | 3.34 | 0.91 | 4 | 4 |
| 6 | 9 | 224 (11.8%) | 294 (12.8%) | 5.23 | 3.90 | 3 | 3 |
| 7 | 3 | 313 (24.1%) | 443 (23.3%) | 5.39 | 5.55 | 4 | 4 |
| 8 | 4 | 275 (30.6%) | 314 (31.4%) | 4.12 | 3.18 | 5 | 4 |
| 9 | 6 | 274 (8.3%) | 386 (9.9%) | 5.08 | 5.74 | 4 | 5 |
| 10 | 8 | 295 (22.7%) | 372 (26.6%) | 4.02 | 3.9 | 5 | 4 |
| 11 | 4 | 219 (16.9%) | 235 (23.5%) | 4.01 | <1 | 8 | 3 |
| 12 | 12 | 272 (20.9%) | 340 (30.9%) | 4.74 | 2.30 | n.a. | 4 |
| 13 | 9 | 435 (33.5%) | 478 (28.1%) | 4.30 | 4.07 | 3 | 4 |
| 14 | 3 | 257 (13.5%) | 274 (13.7%) | 2.05 | 2.90 | 3 | 3 |

TABLE 3

Immunogenicity of HIV-1 anti-Tat immunization in HIV-1 seropositive patients

| Patient code | Immunization type (A/B) | Anti-Tat response antibodies | Anti-Tat antibodies (in units of optical density) Basal | Peak | HSR response | CMI response |
|---|---|---|---|---|---|---|
| 1 | B | Y | 0.240 | 1.230 | n.a. | n.a. |
| 2 | A | Y | 0.104 | 1.526 | n.a. | POS |
| 3 | B | Y | 0.217 | 0.537 | NEG | NEG |
| 4 | B | Y | 0.214 | 1.063 | POS | n.a. |
| 5 | A | Y | 0.446 | 1.612 | n.a. | n.a. |
| 6 | A | Y | 0.213 | 0.664 | NEG | NEG |
| 7 | A | Y | 0.204 | 1.139 | n.a. | n.a. |
| 8 | B | Y | 0.104 | 1.045 | POS | POS |
| 9 | A | Y | 0.422 | 0.812 | NEG | n.a. |
| 10 | B | Y | 0.125 | 1.492 | n.a. | n.a. |
| 11 | A | Y | 0.252 | 0.682 | NEG | n.a. |
| 12 | A | Y | 0.410 | 2.219 | POS | POS |
| 13 | A | Y | 0.162 | 0.508 | POS | POS |
| 14 | B | Y | 0.120 | 2.012 | n.a. | n.a. |

HSR: Delayed hypersensibility
CMI: Cell-mediated immunity

What is claimed is:

1. A protein or a protein fragment which is carboxymethylated and is selected from the group consisting of a viral regulation protein, a fragment of a viral regulation protein, interferon α and a fragment of interferon α, said fragments comprising 8 to 110 amino acids.

2. A protein or a fragment of claim 1, wherein the virus is HIV-1 or HIV-2.

3. A protein or a fragment of claim 1 wherein it is a viral regulation protein or a fragment of a viral regulation protein.

4. A protein or a fragment of claim 1 wherein it comes from Tat.

5. A process for preparing a protein or a fragment of claim 1, comprising subjecting said protein or said fragment to a carboxymethylation step to obtain the expected carboxymethylated protein and isolating the same.

6. The process of claim 5 wherein said protein or said fragment is present as a fused form with a marker (FP) upon the carboxymethylation.

7. The process of claim 6 wherein the marker is cleaved after isolation.

8. The process of claim 6 wherein the marker comprises a peptidic compound comprising several histidines.

9. A protein or a fragment according to claim 1, for its usse in a theraprutic treatment method for the human or animal body.

10. A protein or a fragment of HIV-1 Tat protein carboxymethylated for its use in a therapeutic treatment method for the human or animal body.

11. A pharmaceutical composition containing as an active ingredient at least one of the carboxymethylated proteins or fragments of claim 1, and a pharmaceutically acceptable excipient.

12. A pharmaceutical composition containing as an active ingredient, at least one of the proteins or fragments as defined in claim 2 and a pharmaceutically acceptable excipient.

13. A vaccine containing as an active ingredient at least one of the proteins or fragments of claim 1.

14. A method of immunizing warm-blooded animals to toxins comprising administering to warm-blooded animals in need thereof an immunizing amount of a protein or protein fragment of claim 1.

15. A method of immunizing warm-blooded animals to toxins comprising administering to warm-blooded animals in need thereof an immunizing amount of a protein or protein fragment of claim 3.

* * * * *